ized as a second step to thereby obtain a 2-cyanoimino-1,

United States Patent
Mita et al.

(10) Patent No.: US 6,750,351 B2
(45) Date of Patent: Jun. 15, 2004

(54) METHOD OF PRODUCTION OF 2-CYANOIMINO-1, 3-THIAZOLIDINE

(75) Inventors: Shinya Mita, Toyama (JP); Masahiro Murotani, Toyama (JP); Kenichi Ishii, Uozu (JP)

(73) Assignee: Nippon Carbide Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/297,812

(22) PCT Filed: Dec. 28, 2001

(86) PCT No.: PCT/JP01/11680

§ 371 (c)(1),
(2), (4) Date: Dec. 10, 2002

(87) PCT Pub. No.: WO03/057680

PCT Pub. Date: Jul. 17, 2003

(65) Prior Publication Data

US 2003/0130327 A1 Jul. 10, 2003

(51) Int. Cl.[7] ........................ C07D 277/18; C07C 36/04
(52) U.S. Cl. ....................................................... 548/198
(58) Field of Search ............................... 558/9; 548/198

(56) References Cited

U.S. PATENT DOCUMENTS

| 4,298,544 A | 11/1981 | Robinson |
| 5,208,351 A | 5/1993 | Thalhammer |
| 5,574,165 A * | 11/1996 | Lantzsch ................... 548/198 |

FOREIGN PATENT DOCUMENTS

| DE | 32 25 249 A1 | 5/1983 |
| DE | 3225249 * | 5/1983 |
| DE | 44 27 539 A1 | 2/1996 |
| WO | WO 03/057680 A1 | 7/2003 |

OTHER PUBLICATIONS

International Search Report for PCT/JP01/11680 mailed on Apr. 16, 2002.
International Search Report dated Apr. 16, 2002.

* cited by examiner

Primary Examiner—Rita Desai
Assistant Examiner—Kamal Saeed
(74) Attorney, Agent, or Firm—Rader, Fishman & Grauer PLLC

(57) ABSTRACT

A method for producing high purity 2-cyanoimino-1,3-thiazolidine comprising the steps of:

reacting an alkali metal cyanide compound, an alkali metal hydroxide, a lower alcohol and chlorine in an aqueous solution to form an carboimidic acid ester solution, then adding an organic solvent thereto, followed by adding a cyanamide solution to form an N-cyanocarbonimidic acid ester, and further extracting the resultant ester with an organic solvent extracting solution, followed by washing with an aqueous solution of a reducing agent solution to obtain a high purity, stable N-cyanocarbonimidic acid ester as a first step; and reacting the N-cyanocarbonimidic acid ester obtained in the first step with 2-aminoethanethiol to be cyclicized as a second step to thereby obtain a 2-cyanoimino-1, 3-thiazolidine.

9 Claims, 1 Drawing Sheet

METHOD OF PRODUCTION OF 2-CYANOIMINO-1, 3-THIAZOLIDINE

TECHNICAL FIELD

The present invention relates to a method for industrially producing 2-cyanoimino-1,3-thiazolidine useful as an intermediate material of pharmaceuticals or agrochemicals. More specifically, it relates to a method for producing a high purity 2-cyanoimino-1,3-thiazolidine using a high purity, stable intermediate N-cyanocarbonimidic acid ester, which is obtained from an alkali metal cyanide compound, an alkali metal hydroxide, a lower alcohol, chlorine and cyanamide.

BACKGROUND ART

Several methods have been known for the production of an N-cyanocarbonimidic acid ester. For example, 1) European Patent Publication EP14,064 (A2) (1980), Japanese Unexamined Patent Publication (Kokai) No. 5-186412 (1993), and Japanese Unexamined Patent Publication (Kokai) No. 5-186413 (1993) propose a method for obtaining N-cyanocarbonimidic acid methyl ester from sodium hydroxide and methanol and gaseous state or liquid state chlorocyan/cyanogen chloride and cyanamide. This reaction is believed to be expressed by the following formula:

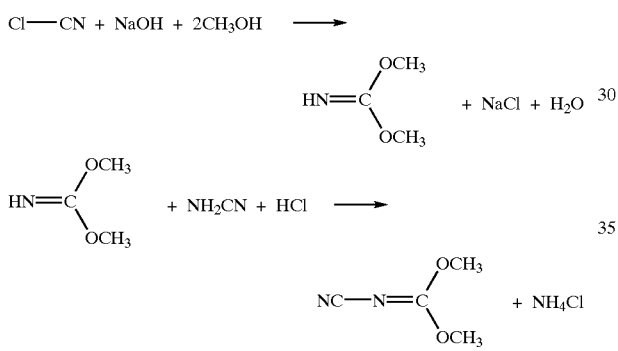

Further, 2) German Patent Publication DE3,225,249 (A1) (1983) proposes a method for obtaining N-cyanocarbonimidic acid methyl ester from sodium cyanide, sodium hydroxide, methanol, chlorine and cyanamide as shown in the following formula:

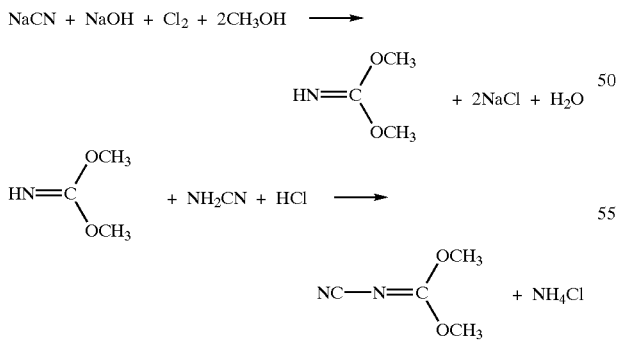

On the other hand, 3) as a method for producing 2-cyanoimino-1,3-thiazolidine, the method of using N-cyanocarbonimidodithioic acid ester is described in *Arch. Pharm.* (Weiheim, Ger.), 305 (10), P731 (1972), Japanese Unexamined Patent Publication (Kokai) No. 48-91064, *Gazz. Chim. Ital.*, 110 (506), P345, WO 92-17462 (1992), etc. This reaction is believed to be expressed by the following formula:

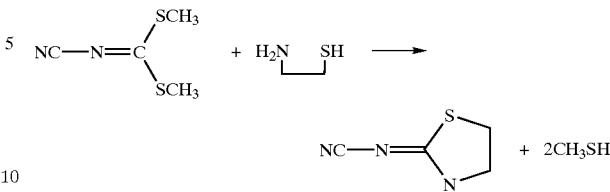

Further, 4) as a method using similar starting materials, there is the disclosure in Japanese Unexamined Patent Publication (Kokai) No. 60-28969 (1985). This reaction is believed to be expressed by the following formula:

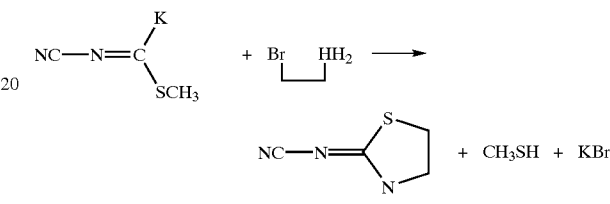

Further, 5) regarding the method of using an N-cyanocarbonimidic acid ester, *J. Heterocycl. Chem.*, 24 (1), P275 (1987) describes a method of using a diphenyl ester. This reaction formula is as follows:

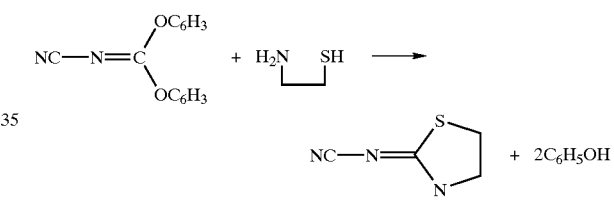

Further, 6) the method of using N-cyanocarbonimidic acid methyl ester is described in *Org. Prep. Proced. Int.*, 26 (6), P721 (1991), German Patent DE4427539 (A1) (1996), and European Patent EP695744 (A1) (1996). This reaction formula is as follows:

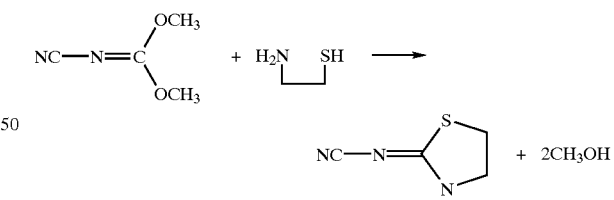

However, in the first proposal of using chlorocyan/cyanogen chloride, it is necessary to handle strongly poisonous chlorocyan/cyanogen chloride starting material as a gas. Special care have to be taken over the material and air-tightness of the system and the treatment facilities for the exhaust, drainage, etc., and therefore the use of this method on an industrial scale was difficult.

Further, also in the second proposal, a stable yield of the formed N-cyanocarbonimidic acid methyl ester could not be expected. Depending on the situation, the yield sometimes extremely decreased. Quality-wise as well, not only the purity is low, but also the stability becomes poor, and furthermore the hygroscopicity is strong and long term storage is not possible, and therefore it is difficult and uneconomical to use this method on an industrial scale.

Further, many N-cyanocarbonimidic acid esters are high in solubility in organic solvents. Accordingly, when concentrating and precipitating a solution containing the same to obtain crystals, the stability is poor and, therefore, the loss in the concentration stage is large and the yield becomes poor. Further, since due to the properties thereof, many esters easily hydrolyze, care is required in the temperature at the time of extraction or separation of liquid. Thus there has been a demand for simply separating and drying the products so as to obtain stable products.

Further, in particular, when methylene chloride is used among the organic solvents, since the boiling point of the methylene chloride is low, there are the problems that the yield is usually only about 50% and the cost of the starting materials becomes high. To raise the yield, special equipment such as a coolant recirculating system becomes necessary and therefore new capital investment is required.

On the other hand, in the third and fourth proposals using another compound, that is, N-cyanocarbonimidodithioic acid ester, as the starting material for the 2-cyanoimino-1,3-thiazolidine, the toxicity or inflammability or odor of the gaseous methyl mercaptan dissociating at the time of the reaction becomes a problem. Further, in the preparation of the compound, there is the problem that carbon disulfide having an extremely high inflammability or toxicity has to be used.

In the case of an N-cyanocarbonimidic acid ester, there are the effects that, since phenol or alcohol is produced as a byproduct, it is easily to recover and recycle and simultaneously the problem of toxicity or odor is eliminated. In the fifth proposal, the diphenoxy compound used is high in the price thereof and difficult to acquire. In the sixth proposal, the purity of the formed 2-cyanoimino-1,3-thiazolidine is low and regardless of the method of production, inherently requiring careful control, the settings of the conditions were insufficient and an industrially stable supply of products was difficult.

DISCLOSURE OF THE INVENTION

Accordingly, the object of the present invention is to solve the above problems in the prior art and to develop a method for safely industrially producing, inexpensive N-cyanocarbonimidic acid ester and 2-cyanoimino-1,3-thiazolidine.

Another object of the present invention is to provide a method for producing an N-cyanocarbonimidic acid ester and 2-cyanoimino-1,3-thiazolidine, as a high quality crystal, with a good yield and high purity.

In accordance with the present invention, it is possible to produce a high purity, stable N-cyanocarbonimidic acid ester by reacting an alkali metal cyanide compound, an alkali metal hydroxide, a lower alcohol and chlorine in an aqueous solution to form an carbonimidic acid ester solution, then adding an organic solvent thereto, followed by adding a cyanamide solution to form an N-cyanocarbonimidic acid ester, and further extracting the resultant ester with an organic solvent extracting solution, followed by washing with an aqueous solution of a reducing agent.

In accordance with the present invention, it is possible to produce high purity 2-cyanoimino-1,3-thiazolidine by reacting the high purity, stable N-cyanocarbonimidic acid ester obtained in the above method with 2-aminoethanethiol to be cyclized, in particular, without complicated purification.

MODE FOR CARRYING OUT THE INVENTION

Figure 1:
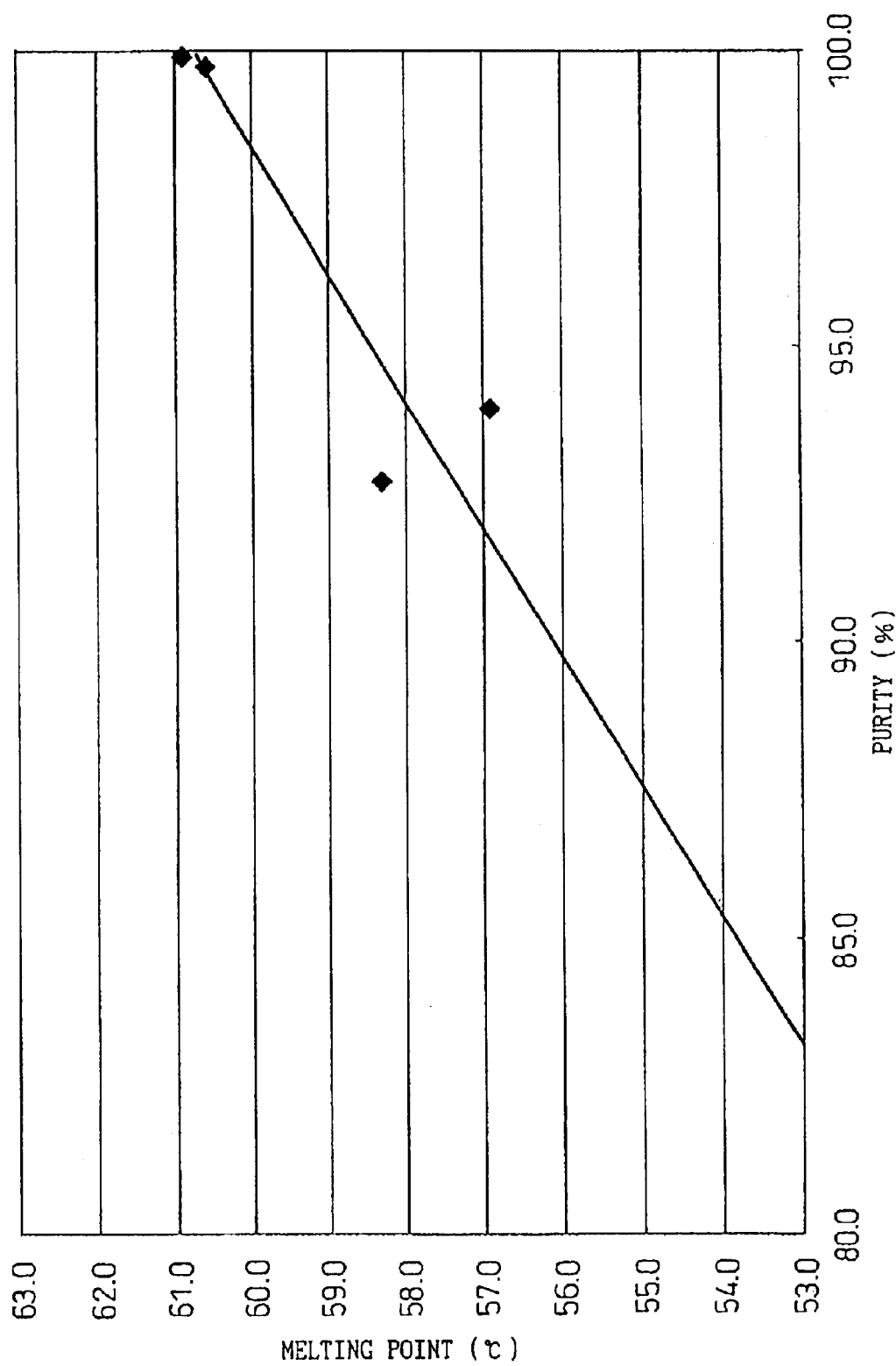
FIG. 1 is a graph showing the relationship between the purity and the melting point of N-cyanocarbonimidic acid methyl ester.

Embodiments of the present invention will be explained in detail below.

According to the present invention, it is possible to produce the intended 2-cyanoimino-1,3-thiazolidine easily and safely, with the use of an alkali metal cyanide compound, an alkali metal hydroxide, a lower alcohol, chlorine and cyanamide to react with 2-aminoethanethiol through an intermediate N-cyanocarbonimidic acid ester.

The first reaction of the present invention is considered to progress by the following formula:

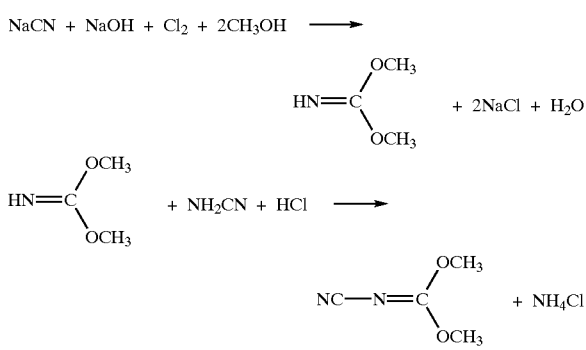

In the present invention, first, the alkali metal cyanide compound, alkali metal hydroxide, and lower alcohol are dissolved in water, then chlorine gas is blown thereto to react and produce an carbonimidic acid ester solution. In this reaction, the alkali metal hydroxide should be added in an amount of preferably 0.5 to 3 equivalents, more preferably 1.0 to 1.2 equivalents, to one mole of the alkali metal cyanide compound. Further, in this reaction, a lower alcohol should be added in an amount of preferably about 2.0 to 5.0 equivalents, more preferably 2.8 to 3.2 equivalents, to one mole of the alkali metal cyanide compound. Further, in this reaction, chlorine should be added in an amount of preferably about 0.5 to 1.5 equivalents, more preferably 0.8 to 1.2 equivalents, to one mole of an alkali metal cyanide compound. When the chlorine is insufficient, the yield is decreased. Even when an excess amount of the chlorine is used, the intermediate tends to break down and become a dialkyl carbonic acid ester and the yield tends to decrease.

Specific examples of the alkali metal cyan compound are sodium cyanate, potassium cyanate, etc., but, from the viewpoint of economy and reactivity, the use of sodium cyanide is preferable.

Specific examples of the alkali metal hydroxide are sodium hydroxide, potassium hydroxide, etc., but, from the viewpoint of economy and reactivity, the use of sodium hydroxide is preferable.

Specific examples of the lower alcohol are methanol, ethanol, normal propanol, isopropanol, etc., but the use of methanol is preferable from the viewpoint of economy and reactivity.

The temperature of this reaction may be suitably selected from the viewpoint of the suppression of decomposition of the starting materials or imide carbonate ester formed and secondary reactions, but −5° C. to 10° C. is most preferable.

The reaction time is not particularly limited, but is preferably 5 to 20 hours, more preferably 6 to 10 hours.

In the present invention, an organic solvent is added to the carbonimidic acid ester solution, then cyanamide is added in an amount of preferably about 0.2 to 1.0 mole, more preferably 0.7 to 0.8 mole, to one mole of the alkali metal cyanide compound so as to produce an carbonimidic acid ester solution. At this time, an acid is preferably used to control the pH to 6.7 to 7.0.

The cyanamide used in this reaction can be added as a crystal or solution. The solvent, when it is used as a solution, is not particularly limited if the solvent can dissolve the starting materials and does not react with the reaction starting materials and reaction intermediates, but water is preferably used in view of its low price and high safety. At that time, the concentration of cyanamide is preferably about 5 to 100% by weight, more preferably 10 to 60% by weight.

The reaction temperature of the reaction is not particularly limited, but the reaction can be preferably performed at 30° C., or less but 10 to 25° C. is most preferable from the viewpoint of the reaction speed, the suppression of the decomposition of the starting materials or N-cyanocarbonimidic acid ester formed, etc. The time of addition of the cyanamide is not particularly limited, but preferably is 1 to 10 minutes, more preferably 2 to 5 minutes. Further, as the aging time, the reaction should be completed in 1 to 5 hours and more preferably 2 to 3 hours.

Specific examples of the acid for the control of the pH are hydrochloric acid, sulfuric acid, nitric acid, carbonic acid, phosphoric acid, etc., but it is preferable to use hydrochloric acid or sulfuric acid from the viewpoint of economy.

After the reaction is completed, the oil layer is separated and is extracted one to five times using an equal weight or two times the weight of the organic solvent based upon the reaction solution.

Specific examples of the organic solvent for the extract of the N-cyanocarbonimidic acid ester are methylene chloride, chloroform, carbon tetrachloride, benzene, toluene, xylene, methyl acetate, ethyl acetate, etc. From the viewpoint of stability considering the temperature at the time of recovery or the economy considering the facility for concentration and from the extraction efficiency, the use of chloroform is preferable. The extraction temperature is not particularly limited, but it is possible to carry out the extraction at a temperature of 25° C. or less, and 0 to 15° C. is most preferable from the viewpoint of the extraction speed, the suppression of the decomposition of the starting materials or the formed N-cyanimide carbonate ester or secondary reactions, etc. The extraction time is not particularly limited, but preferably is 30 minutes to 2 hours, more preferably 30 minutes to 1 hour.

In the present invention, the extracted N-cyanimide carbonate ester is then washed with an aqueous solution of a reducing agent and dehydrated. Due to this treatment, not only is it possible to ensure the stability of the N-cyanocarbonimidic acid ester in the manufacturing process, but also it is possible to obtain a stable, high purity final product.

Specific examples of the reducing agent for the washing are sodium hydrogensulfite, sodium sulfite, sodium thiosulfate, etc., but from the viewpoint of the economy considering the stability in an aqueous solution or reducing ability, sodium hydrogensulfite or sodium sulfite is desirable.

Further, the concentration and amount of the use of the aqueous solution of the reducing agent for the washing is not particularly limited, but the concentration of the aqueous solution of 1 to 50% by weight and the use of 1/20 to 1/2 of the weight of the extract are preferable, but from the viewpoint of the volumetric efficiency, the suppression of the load on the treatment of the wastewater, etc., the washing is most preferably carried out at a concentration of the aqueous solution of 2 to 10% by weight and using 1/10 to 1/5 of the weight of the extract.

The temperature of this washing is not particularly limited, but the washing is preferably suitably performed at a temperature of not more than 25° C. From the viewpoint of the suppression of the decomposition of the materials or produced N-cyanocarbonimidic acid ester and secondary reactions etc., 0 to 15° C. is most preferable. The extraction time is not particularly limited, but is preferably 30 minutes to 2 hours, more preferably 40 minutes to 1 hour.

On the other hand, Specific examples of the desiccant for the dehydration treatment are sodium sulfate, magnesium sulfate, calcium chloride, a molecular sieve, etc., but from the viewpoint of economy considering the efficiency of dehydration or solubility in the extract, the use of a molecular sieve is desirable. In particular, it is possible to use Molecular Sieve (3A).

These extracts are concentrated in vacuo. After concentrated, the concentrate is gradually cooled to a temperature of, for example, 5° C. or less to precipitate a crystal of N-cyanocarbonimidic acid ester. The slurry is separated. The yield of the crystal thus obtained is usually at least 60% (based on alkali metal cyanide compound). The purity is at least 99% (purity measured by HPLC method). Further, the rate of production, including the filtrate, is at usually at least 90% (based on alkali metal cyanide compound).

The temperature for the concentration is not particularly limited, but the concentration may be suitably carried out at 50° C. or less. The use of a temperature of 35 to 45° C. is most preferable from the viewpoint of the extraction speed, suppression of the decomposition of the starting materials or the formed N-cyanocarbonimidic acid ester and secondary reactions, etc. The concentration time is not particularly limited, but preferably is 30 minutes to 10 hours, more preferably 4 hours to 7 hours.

Further, the filtrate after separation can be recycled as it is for the extraction of the next reaction.

It is essential that the above crystal is dried by completely removing the organic solvent at the same time as the drying using a box type drier, fluidized drier, flash drier, or other known drier, in particular when used for the next reaction. In particular, when used as a material for the below-mentioned 2-cyanoimino-1,3-thiazolidine, even if remaining in an amount on the order of several percent, sometimes no product is obtained at all.

The drying conditions differ depending on the drier, but when using a box type drier, from the viewpoint of the dehydration speed and prevention of decomposition of the N-cyanocarbonimidic acid ester anhydride, the solution is preferably dried at a drying temperature of 10 to 80° C., more preferably 30 to 50° C., for preferably a drying time of 30 minutes to 10 hours, more preferably 1 to 8 hours.

The second reaction of the present invention is believed to proceed as in the following formula:

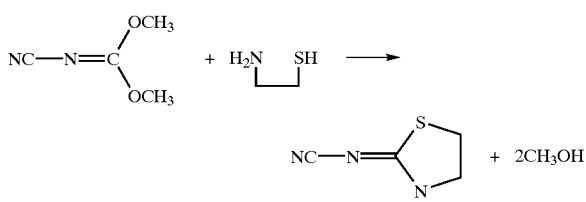

In the present invention, a 2-aminoethanethiol mineral acid salt is added to an alkali aqueous solution to react with the N-cyanocarbonimidic acid ester formed from the above reaction.

As the 2-aminoethanethiol salt, a hydrochloride, sulfate, nitrate, carbonate, acetate, etc. may be used, but from the reactivity, the use of a mineral acid salt is preferable. A hydrochloride is more preferable from the viewpoint of the solubility, economy, etc.

Further, as the alkali used for the neutralization, sodium hydroxide, potassium hydroxide, etc. may be used, but sodium hydroxide is preferable from the viewpoint of economy and reactivity.

The preferable addition amount of alkali to the 2-aminoethanethiol salt is 1.9 to 2.1 equivalents per mole of the 2-aminoethanethiol salt, more preferably 1.95 to 2.05 equivalents.

Further, instead of a 2-aminoethanethiol, it is possible to use the free compound for the reaction. In this case, it is also possible to use the same in the form of a solution. The preferable amount of alkali added to the 2-aminoethanethiol is 0.9 to 1.1 equivalents per mole of the 2-aminoethanethiol salt, more preferably 0.95 to 1.05 equivalents.

The 2-aminoethanethiol solution used was obtained by using the same solvent as the reaction solvent or a solvent miscible with the reaction solvent and adjusted to a concentration of 20 to 30% by weight.

The reaction temperature, when adding an N-cyanocarbonimidic acid ester, is preferably 20° C. or less from the viewpoint of prevention of decomposition of the N-cyanocarbonimidic acid ester solution. If considering the reaction speed, 0C to 10° C. is further preferred. The preferable reaction time is 20 minutes to 3 hours.

In the present invention, the pH of the above reaction solution is adjusted with an acid, then heated to carry out a desired cyclization reaction to obtain a crystal of the intended 2-cyanoimino-1,3-thiazolidine. This cyclization reaction is preferably carried out at a pH of 10 to 11, more preferably a pH of 10.2 to 10.6.

The acid usable for the adjustment of pH is not particularly limited, but mineral acids such as hydrochloric acid, sulfuric acid, nitric acid may be exemplified. The use of various types of solvents is also possible, but the use of hydrochloric acid is preferable from the viewpoint of the reactivity, easy availability, having, etc. This reaction is carried out by adding an acid of a concentration of, for example, 5 to 100% by weight at a speed maintaining a reaction temperature of 10 to 30° C., more preferably a reaction temperature of 15 to 25° C.

The reaction temperature of the cyclization reaction is preferably a temperature of 45° C. or less from the viewpoint of prevention of polymerization and other secondary reactions. Considering the reaction speed, a temperature of 35 to 40° C. is further preferable. The reaction time is not particularly limited, but is preferably 5 to 15 hours, more preferably 7 to 10 hours.

After the end of the reaction, the reaction solution is gradually cooled to, for example, a temperature of 15° C. or less and adjusted in pH, then the crystal of 2-cyanoimino-1,3-thiazolidine is precipitated. The pH is adjusted to preferably a pH of 5.5 to 7.5, more preferably a pH of 6.6 to 7.0. The acid usable for adjusting the pH is not particularly limited. For example, mineral acids such as hydrochloric acid, sulfuric acid, nitric acid, may be exemplified. Various solutions may be used, but the use of hydrochloric acid is preferably from the viewpoint of the reactivity or easy availability. This slurry solution is cooled to a temperature of, for example, 15° C. or less, then the slurry is separated. The yield of the crystal of 2-cyanoimino-1,3-thiazolidine thus obtained is usually at least 80% (based on cyanamide) and the purity at least 99% (measured by HPLC).

The drying conditions differ depending on the drier, but when using a box type drier, from the viewpoint of the prevention of decomposition of the 2-cyanoimino-1,3-thiazolidine, the solution is preferably dried at a drying temperature of 60 to 80° C., more preferably 65 to 75° C., for preferably a drying time of 30 minutes to 48 hours, more preferably 8 to 16 hours.

EXAMPLES

The present invention will be explained in more detail by the following Examples, but the present invention is, of course, not limited to these Examples.

Example 1

A 1000 ml four-necked flask provided with a thermometer and stirring device was charged with 108 g (6.0 moles) of water. While stirring, 256.0 g (1.6 moles) of a 25% by weight aqueous solution of sodium hydroxide and 70.9 g (1.5 moles) of sodium cyanide were added. While maintaining the temperature at 5° C. or less, chlorine gas (1.5 moles) was reacted over 6 hours. After the end of the reaction, the residual chlorine gas was exhausted outside of the system by nitrogen gas. Next, while maintaining the temperature of 5° C. or less, a 36% by weight aqueous solution of hydrochloric acid was added, the pH was adjusted to 7.0, then 350 ml (2.0 moles) of chloroform was added.

142.0 g (0.85 mole) of a 25% by weight aqueous solution of cyanamide was added and a 36% by weight aqueous solution of hydrochloric acid was gradually added, whereby a reaction was carried out for 2 hours, while adjusting the pH to 6.6 to 7.0. Next, the aqueous layer was extracted two times with 300 ml (1.7 moles) of chloroform.

The chloroform solution thus obtained was rinsed twice with 200 g (0.07 mole) of a 5% by weight aqueous solution of sodium hydrogensulfite, then dehydrated with 5.0 g of Molecular Sieve 3A. The molecular sieve was filtered out, then the solution was concentrated in vacuo, whereby a white crystal was obtained. This was filtered by suction filtration to obtain 63.1 g of wet crystal of N-cyanocarbonimidic acid methyl ester. The resultant crystal was dried in vacuo at 40° C. for 5 hours to obtain 62.1 g of N-cyanocarbonimidic acid methyl ester having a purity of 99.7% (yield 63.5%=converted value of purity from cyanamide (Note: the same below)). The melting point of the N-cyanocarbonimidic acid methyl ester thus obtained was 61° C. The relationship between the purity and the melting point is shown in FIG. 1. Then, the changes in purity of the N-cyanocarbonimidic acid methyl ester over time were tested by the following method.

That is, a 50 ml sample flask was charged with 10 g of N-cyanocarbonimidic acid methyl ester having a purity of 99.7%, sealed, then stored in a 25° C. thermostat. After about 3 months, the flask was taken out and the purity analyzed. The results are shown in Table I.

Note that the filtrate the obtained weighed 65.4 g. The concentration of the N-cyanocarbonimidic acid methyl ester in the solution was 30.4%. The value corresponds to 20.0% converted to yield.

A 300 ml four-necked flask provided with a thermometer and stirring device was charged with 100 ml (2.9 moles) of water. While stirring, 83.2 g (0.5 mole) of a 25% by weight aqueous solution of sodium hydroxide was added, then 28.6 g (0.25 mole) of 2-aminoethanethiol hydrochloride was added and the solution heated and dissolved at 30° C. Next, while maintaining the temperature at 5° C. or less, 28.6 g (0.25 mole) of the N-cyanocarbonimidic acid methyl ester was added and a reaction is carried out for 2 hours. Next, the solution was warmed to 20° C., the pH was adjusted to 10.5 with a 36% by weight aqueous solution of hydrochloric acid, then a reaction was carried out at 40° C. for 8 hours.

After the end of the reaction, the solution was cooled to a temperature of 10° C., the pH was adjusted to 4.5 with a 36% by weight aqueous solution of hydrochloric acid, then the solution was filtered by suction filtration to obtain 38.9 g of 2-cyanoimino-1,3-thiazolidine. This was dried in vacuo at 70° C. for 8 hours to obtain 2-cyanoimino-1,3-thiazolidine having a purity of 99.7% at a yield of 88.0% (based on charged methyl N-cyanoimide carbonate).

Example 2

A reaction and extraction were carried out in the same way as in Example 1, then the filtrate of Example 1 was mixed in the extract and the mixture was similarly concentrated, precipitated, and dried to obtain 78.2 g of N-cyanocarbonimidic acid methyl ester having a purity of 99.9%. The yield from the cyanamide was 80.7%. The melting point of the N-cyanocarbonimidic acid methyl ester thus obtained was 61° C. The relationship between the purity and the melting point is shown in FIG. 1. Next, the changes in purity are shown in Table I.

Note that the filtrate obtained in Example 2 weighed 71.5 g. The concentration of the N-cyanocarbonimidic acid methyl ester in the solution was 29.8%. The value corresponds to 25.3% converted to yield.

A 300 ml four-necked flask provided with a thermometer and stirring device was charged with 100 ml (2.9 moles) of water. While stirring, 83.2 g (0.5 mole) of a 25% by weight aqueous solution of sodium hydroxide was added, then 28.6 g (0.25 mole) of 2-aminoethanethiol hydrochloride was added and the solution heated and dissolved to 30° C. Next, while maintaining the temperature at 5° C. or less, 28.6 g (0.25 mole) of the N-cyanocarbonimidic acid methyl ester was added and a reaction is carried out for 2 hours. Next, the solution was warmed to 20° C., the pH was adjusted to 10.5 with a 36% by weight aqueous solution of hydrochloric acid, then a reaction was carried out at 40° C. for 8 hours.

After the end of the reaction, the solution was cooled to a temperature of 10° C., the pH was adjusted to 4.5 with a 36% by weight aqueous solution of hydrochloric acid, then the solution was filtered by suction filtration to obtain 38.9 g of 2-cyanoimino-1,3-thiazolidine. This was dried in vacuo at 70° C. for 8 hours to obtain 2-cyanoimino-1,3-thiazolidine having a purity of 99.7% at a yield of 88.0% (based on charged N-cyanocarbonimidic acid methyl ester).

Comparative Example 1

A 1000 ml four-necked flask provided with a thermometer and stirring device was charged with 108 g (6.0 moles) of water. While stirring, 240.0 g (1.5 moles) of a 25% by weight aqueous solution of sodium hydroxide and 68.6 g (1.4 moles) of sodium cyanide were added. While maintaining the temperature at 5° C. or less, chlorine gas (1.5 moles) was reacted over 6 hours. After the end of the reaction, the residual chlorine gas was exhausted outside of the system with nitrogen gas. Next, the pH was adjusted to 7.0 with a 36% by weight aqueous solution of hydrochloric acid, then 350 ml (2.0 moles) of chloroform was added.

155.0 g (1.0 mole) of a 27% by weight aqueous solution of cyanamide and 53.7 g (0.53 mole) of a 36% by weight aqueous solution of hydrochloric acid were added (the pH at that time being 6.6) and a reaction was carried out for 2 hours, then this was separated and the aqueous layer was extracted two times with 300 ml (1.7 moles) of chloroform. The obtained chloroform solution thus obtained was concentrated in vacuo and cooled to obtain a white crystal. This was filtered by suction filtration to obtain 38.8 g of wet crystal of N-cyanocarbonimidic acid methyl ester. This was dried in vacuo at 40DC for 5 hours to obtain 34.8 g of N-cyanocarbonimidic acid methyl ester having a purity of 92.8% (yield 28.3%). The melting point of the N-cyanocarbonimidic acid methyl ester thus obtained was 58° C. The relationship between the purity and the melting point is shown in FIG. 1. Next, the changes in purity are shown in Table I.

A 300 ml four-necked flask provided with a thermometer and stirring device was charged with 100 ml (2.9 moles) of water. While stirring, 83.2 g (0.5 mole) of a 25% by weight aqueous solution of sodium hydroxide was added, then 28.6 g (0.25 mole) of 2-aminoethanethiol hydrochloride was added and the solution was heated and dissolved at 30° C. Next, while maintaining the temperature at 5° C. or less, 20.5 g (0.18 mole) of the N-cyanocarbonimidic acid methyl ester was added and a reaction was carried out for 2 hours. Next, the solution was warmed to 20° C., the pH was adjusted to 9.5 with a 36% by weight aqueous solution of hydrochloric acid, then a reaction was carried out at 40° C. for 8 hours, but polymerization occurred in 2 hours of time and the reaction ended in failure.

Comparative Example 2

A 1000 ml four-necked flask provided with a thermometer and stirring device was charged with 108 g (6.0 moles) of water. While stirring, 256.0 g (1.6 moles) of a 25% by weight aqueous solution of sodium hydroxide and 70.9 g (1.5 moles) of sodium cyanide were added. While maintaining the temperature at 5° C. or less, chlorine gas (1.5 moles) was reacted over 6 hours. After the end of the reaction, the residual chlorine gas was exhausted outside of the system by nitrogen gas. Then, while holding maintaining the temperature at 5° C. or less, a 36% by weight aqueous solution of hydrochloric acid was added, the pH was adjusted to 7.0, then 350 ml (2.0 moles) of chloroform was added.

142.0 g (0.85 mole) of a 25% by weight aqueous solution of cyanamide was added and a reaction was carried out for 2 hours while adjusting the pH to 6.6 to 7.0 with a 36% by weight aqueous solution of hydrochloric acid, then separated and the aqueous layer was extracted two times with 300 ml (1.7 moles) of chloroform. The chloroform solution thus obtained was dehydrated with 5.0 g of Molecular Sieve 3A. The solution was filtered by the molecular sieve, then concentrated in vacuo and cooled to obtain a white crystal. This was filtered by suction filtration to obtain 77.1 g of wet crystal of methyl N-cyanocarbonimidic acid methyl ester. This was dried in vacuo at 40° C. for 5 hours to obtain 71.8 g of N-cyanocarbonimidic acid methyl ester having a purity of 94.0% (yield 69.7%). The yield from the cyanamide was 80.7%. The melting point of the N-cyanocarbonimidic acid methyl ester thus obtained was 56.9° C. The relationship between the purity and the melting point is shown in FIG. 1. Next, the changes in purity are shown in Table I.

A 300 ml four-necked flask provided with a thermometer and stirring device was charged with 100 ml (2.9 moles) of water. While stirring, 83.2 g (0.5 mole) of a 25% by weight aqueous solution of sodium hydroxide was added, then 28.6 g (0.25 mole) of 2-aminoethanethiol hydrochloride was added and the solution heated and dissolved at 30° C. Then, while maintaining the temperature at 5° C. or less, 30.4 g (0.25 mole) of the N-cyanocarbonimidic acid methyl ester was added and a reaction was carried out for 2 hours. Next, the solution was warmed to 20° C., the pH was adjusted to 9.5 with a 36% by weight aqueous solution of hydrochloric acid, then the solution was warmed to 40° C., the pH was adjusted to 9.0 with or 36% by weight aqueous solution of hydrochloric acid, a reaction was carried out for 8 hours.

After the end of the reaction, the solution was cooled to a temperature of 10° C., the pH was adjusted to 6.0 with a 36% by weight aqueous solution of hydrochloric acid, then the solution was filtered by suction filtration to obtain 35.4 g of 2-cyanoimino-1,3-thiazolidine. This was dried in vacuo at 70° C. for 8 hours to obtain 25.1 g having a purity of 90.3% (at a yield of 70.5%, based on the charged N-cyanocarbonimidic acid methyl ester).

TABLE I

Change of Purity of N-cyanocarbonimidic Acid Methyl Ester Along With Time

| | No. of days elapsed (days) | | |
|---|---|---|---|
| | 0 | 180 | Remarks |
| Purity of N-cyanocarbonimidic acid methyl ester (%) | 99.7 | 98.9 | Ex. 1 |
| | 99.9 | 98.1 | Ex. 2 |
| | 92.8 | 88.8 | Comp. Ex. 1 |
| | 94.0 | 91.0 | Comp. Ex. 2 |

Industrial Applicability

According to the method of the present invention, in the practice of 2-cyanoimino-1,3-thiazolidine on an industrial scale, it is possible to solve the various problems of the conventional methods, that is, the hazard of the by-products, the higher cost of the manufacturing facilities etc. accompanying this, and the insufficient yield and produce the desired compound, that is, 2-cyanoimino-1,3-thiazolidine, on an industrial scale with the use of a high purity N-cyanocarbonimidic acid ester.

What is claimed is:

1. A method for producing high purity 2-cyanoimino-1,3-thiazolidine comprising the steps of:

reacting an alkali metal cyanide compound, an alkali metal hydroxide, a lower alcohol and chlorine in an aqueous solution to form an carboimidic acid ester solution, then adding an organic solvent thereto, followed by adding a cyanamide solution to form an N-cyanocarbonimidic acid ester, and further extracting the resultant ester with an organic solvent extracting solution, followed by washing with an aqueous solution of a reducing agent, whereby a high purity, stable N-cyanocarbonimidic acid ester is obtained as a first step; and reacting the N-cyanocarbonimidic acid ester obtained in the first step with 2-aminoethanethiol to be cyclicized as a second step to thereby obtain a 2-cyanoimino-1,3-thiazolidine.

2. A method of production as claimed in claim 1, wherein a molar ratio of the alkali metal cyanide compound and the cyanamide is 1:1 to 0.2.

3. A method of production as claimed in claim 1, wherein the cyanamide is reacted, while controlling the pH of the carboimidic acid ester solution to 6.7 to 7.0.

4. A method of production as claimed in claim 1, wherein the organic solvent is chloroform.

5. A method of production as claimed in claim 1, wherein the reducing agent is at least one reducing agent selected from the group consisting of sodium hydrogensulfite, sodium sulfite, and sodium thiosulfate.

6. A method for producing an N-cyanocarbonimidic acid ester comprising the steps of:

reacting an alkali metal cyanide compound, an alkali metal hydroxide, a lower alcohol and chlorine in an aqueous solution to form an carboimidic acid ester solution;

then adding an organic solvent thereto, followed by adding a cyanamide solution to forms an N-cyanocarbonimidic acid ester; and further extracting the resultant ester with an organic solvent extracting solution, followed by washing with an aqueous solution of a reducing agent.

7. A method of production as claimed in claim 6, wherein a mother liquor after producing the N-cyanocarbonimidic acid ester is mixed and recycled to the extracting solution for the N-cyanocarbonimidic acid ester.

8. A method of production as claimed in claim 1, wherein the purity of the washed high purity, stable N-cyanocarbonimidic acid ester is at least 99%.

9. A method of production as claimed in claim 6, wherein the purity of the washed high purity, stable N-cyanocarbonimidic acid ester is at least 99%.

* * * * *